United States Patent
Boyle

(10) Patent No.: US 10,398,830 B2
(45) Date of Patent: Sep. 3, 2019

(54) DEVICE FOR IN VIVO DELIVERY OF BIOACTIVE AGENTS AND METHOD OF MANUFACTURE THEREOF

(75) Inventor: Christopher T. Boyle, San Antonio, TX (US)

(73) Assignee: Vactronix Scientific, LLC, Freemont, CA (US)

( * ) Notice: Subject to any disclaimer, the term of this patent is extended or adjusted under 35 U.S.C. 154(b) by 0 days.

(21) Appl. No.: 10/258,087

(22) PCT Filed: Nov. 19, 2001

(86) PCT No.: PCT/US01/44642
§ 371 (c)(1),
(2), (4) Date: Aug. 19, 2003

(87) PCT Pub. No.: WO02/060506
PCT Pub. Date: Aug. 8, 2002

(65) Prior Publication Data
US 2004/0024449 A1    Feb. 5, 2004

Related U.S. Application Data

(63) Continuation-in-part of application No. 09/716,146, filed on Nov. 17, 2000, now Pat. No. 8,252,044.

(51) Int. Cl.
*A61F 2/86* (2013.01)
*A61M 5/14* (2006.01)

(52) U.S. Cl.
CPC .............. *A61M 5/14* (2013.01); *A61F 2/86* (2013.01); *A61F 2210/0076* (2013.01); *A61F 2250/0068* (2013.01)

(58) Field of Classification Search
CPC ............. A61F 2250/0068; A61F 2250/0067
USPC ................ 623/1.27, 1.39–1.48, 1.15–1.16
See application file for complete search history.

(56) References Cited

U.S. PATENT DOCUMENTS

| | | | |
|---|---|---|---|
| 3,797,485 A | 3/1974 | Urquhart | 128/213 |
| 4,203,442 A | 5/1980 | Michaels | 128/260 |
| 4,309,776 A | 1/1982 | Berguer | 3/1 |
| 4,464,450 A | 8/1984 | Teuscher | 430/59 |
| 4,479,796 A | 10/1984 | Kallok | 604/93 |

(Continued)

FOREIGN PATENT DOCUMENTS

| | | | |
|---|---|---|---|
| EP | 0 528 039 | 11/1991 | A61L 27/00 |
| EP | 0 850 604 | 7/1998 | A61F 2/06 |

(Continued)

OTHER PUBLICATIONS

European Search Report, pp. 1-7 (dated Feb. 23, 2011).
Extended European Search Report, pp. 1-6 (dated Nov. 10, 2014).

*Primary Examiner* — Jacqueline Woznicki
(74) *Attorney, Agent, or Firm* — David G. Rosenbaum; Benjamin D. Rotman; Rosenbaum IP, P.C.

(57) ABSTRACT

The present invention consists of an implantable structural element for in vivo delivery of bioactive active agents to a situs in a body. The implantable structural element may be configured as an implantable prosthesis, such as an endoluminal stent, cardiac valve, osteal implant or the like, which serves a dual function of being prosthetic and a carrier for a bioactive agent. Alternatively, the implantable structural element may simply be an implantable article that serves the single function of acting as a time-release carrier for the bioactive agent.

6 Claims, 6 Drawing Sheets

(56) References Cited

U.S. PATENT DOCUMENTS

| | | | |
|---|---|---|---|
| 5,002,661 A | 3/1991 | Chick et al. ............... 210/192 |
| 5,062,829 A | 11/1991 | Pryor et al. ................ 604/57 |
| 5,180,366 A | 1/1993 | Woods ...................... 604/96 |
| 5,295,962 A | 3/1994 | Crocker et al. .............. 604/101 |
| 5,304,121 A | 4/1994 | Sahatjian ................... 604/53 |
| 5,370,681 A | 12/1994 | Herweck et al. ............. 623/1 |
| 5,411,550 A | 5/1995 | Herweck et al. ............. 623/1 |
| 5,441,515 A | 8/1995 | Khosravi et al. ............ 606/194 |
| 5,443,496 A | 8/1995 | Schwartz et al. ............ 623/1 |
| 5,449,382 A | 9/1995 | Dayton ..................... 623/1 |
| 5,607,463 A * | 3/1997 | Schwartz ............ A61L 27/306 623/1.44 |
| 5,609,629 A | 3/1997 | Fearnot et al. .............. 623/1 |
| 5,824,049 A * | 10/1998 | Ragheb et al. .............. 623/1.44 |
| 5,843,172 A * | 12/1998 | Yan ...................... A61F 2/82 604/104 |
| 5,972,027 A | 10/1999 | Johnson .................... 623/1 |
| 6,071,305 A | 6/2000 | Brown et al. ............... 623/1 |
| 6,099,562 A | 8/2000 | Ding et al. ................. 623/1.46 |
| 6,143,370 A | 11/2000 | Panagiotou ................. 427/422 |
| 6,187,370 B1 | 2/2001 | Dinh et al. ................. 427/2.24 |
| 6,202,304 B1 | 3/2001 | Shatz ...................... 29/896.6 |
| 6,203,536 B1 | 3/2001 | Berg et al. ................. 604/500 |
| 6,228,423 B1 | 5/2001 | Sokoll et al. ............... 427/213.3 |
| 6,240,616 B1 | 6/2001 | Yan ........................ 29/527.2 |
| 6,254,632 B1 * | 7/2001 | Wu et al. ................... 623/1.15 |
| 6,273,908 B1 | 8/2001 | Ndondo-Lay ............... 623/1 |
| 6,284,305 B1 | 9/2001 | Ding et al. ................. 427/1 |
| 6,287,628 B1 | 9/2001 | Hossainy et al. ............. 427/2.3 |
| 6,358,556 B1 | 3/2002 | Ding et al. ................. 427/2.24 |
| 6,379,381 B1 * | 4/2002 | Hossainy ............ A61L 31/146 623/1.15 |
| 6,379,382 B1 | 4/2002 | Yang ....................... 623/1.42 |
| 6,387,121 B1 | 5/2002 | Alt ......................... 623/1.15 |
| 6,395,326 B1 * | 5/2002 | Castro ............... A61L 31/10 427/2.24 |
| 6,399,144 B2 | 6/2002 | Dinh et al. ................. 427/2.24 |
| 6,641,607 B1 * | 11/2003 | Hossainy et al. ............. 623/1.15 |
| 6,709,379 B1 | 3/2004 | Brandau et al. .............. 600/3 |
| 6,758,859 B1 * | 7/2004 | Dang ................. A61F 2/91 623/1.15 |
| 2001/0000802 A1 | 5/2001 | Soykan et al. ............... 623/1.13 |
| 2001/0020151 A1 | 9/2001 | Reed et al. ................. 604/103.02 |
| 2002/0007209 A1 | 1/2002 | Scheerder et al. ............ 623/1.15 |
| 2002/0042645 A1 | 4/2002 | Shannon .................... 623/1.13 |
| 2002/0082679 A1 * | 6/2002 | Sirhan .................. A61F 2/91 623/1.15 |
| 2002/0082680 A1 * | 6/2002 | Shanley et al. .............. 623/1.16 |
| 2002/0091440 A1 | 7/2002 | Calcote .................... 623/1.42 |
| 2002/0115986 A1 | 8/2002 | Shadduck ................... 604/891.1 |
| 2003/0018381 A1 * | 1/2003 | Whitcher et al. ............. 623/1.15 |
| 2003/0060871 A1 * | 3/2003 | Hill ..................... A61F 2/07 623/1.15 |
| 2006/0129231 A1 * | 6/2006 | De Scheerder et al. ..... 623/1.16 |

FOREIGN PATENT DOCUMENTS

| | | | |
|---|---|---|---|
| EP | 1 132 058 | 3/2000 | ............ A61F 2/06 |
| EP | 0 875 218 | 2/2005 | ............ A61F 31/00 |
| JP | 09-099056 | 4/1997 | ............ A61L 31/00 |
| WO | WO 97/46268 | 12/1997 | ............ A61L 29/00 |
| WO | 98/13537 | 4/1998 | ............ C25D 1/00 |
| WO | WO 1998/023228 | 6/1998 | ............ A61F 2/06 |
| WO | 98/58600 | 12/1998 | ............ A61F 2/06 |
| WO | 00/18327 | 4/2000 | ............ A61F 2/06 |
| WO | 00/25841 | 5/2000 | ............ A61L 31/14 |
| WO | WO 00/74584 | 12/2000 | ............ A61B 19/00 |
| WO | WO 01/12158 | 2/2001 | ............ A61M 31/00 |
| WO | WO 01/17577 | 3/2001 | ............ A61L 31/14 |
| WO | WO 2001/017577 | 3/2001 | ............ A61L 31/14 |
| WO | 01/66036 | 9/2001 | ............ A61F 2/06 |
| WO | WO 2002/060506 | 8/2002 | ............ A61L 27/04 |
| WO | WO 2003/028244 | 2/2003 | ............ A61L 2/06 |

* cited by examiner

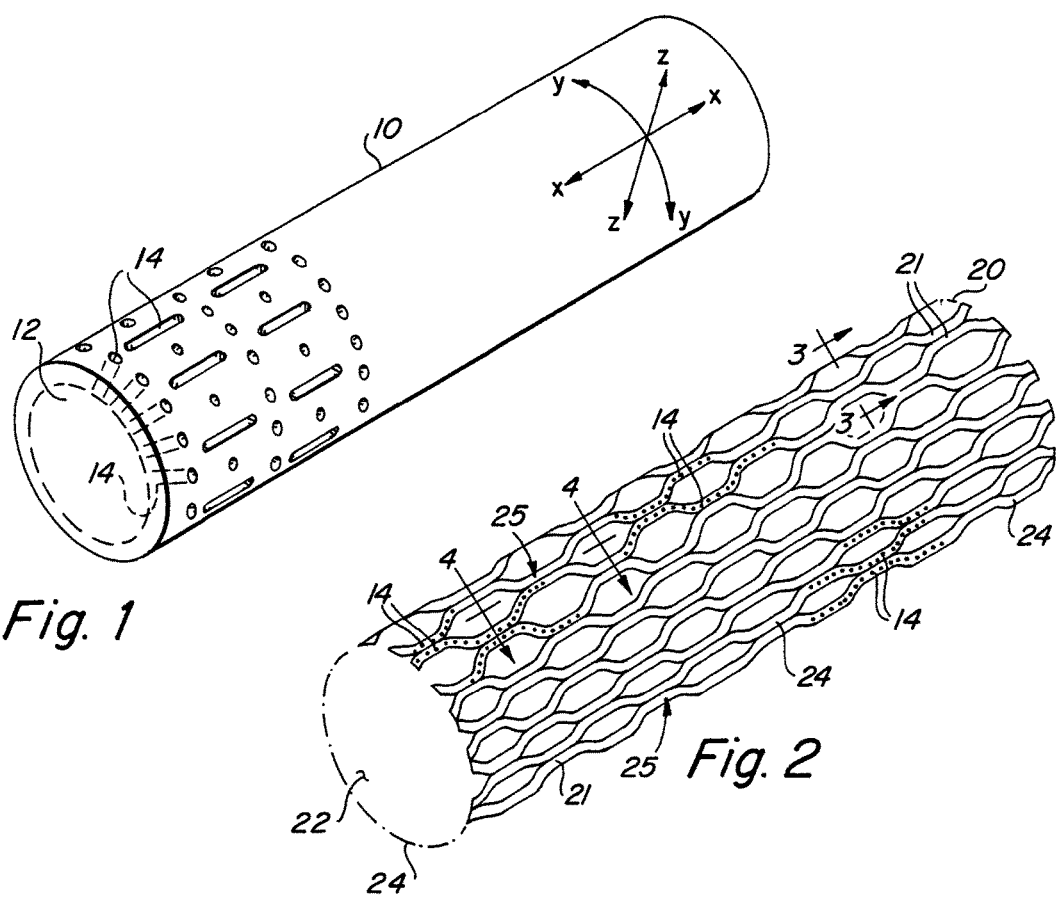
Fig. 1
Fig. 2
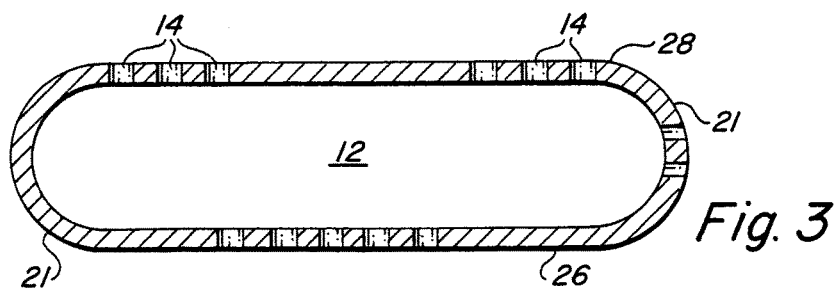
Fig. 3
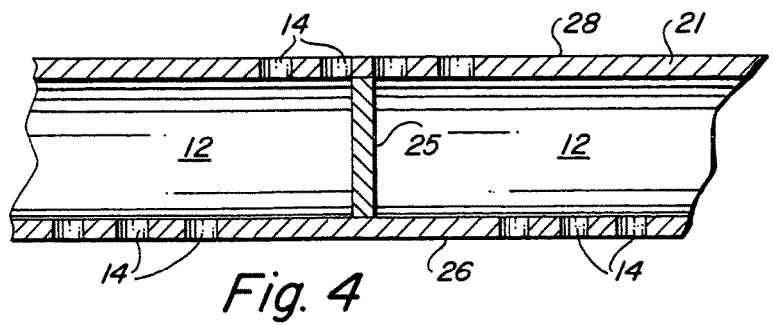
Fig. 4

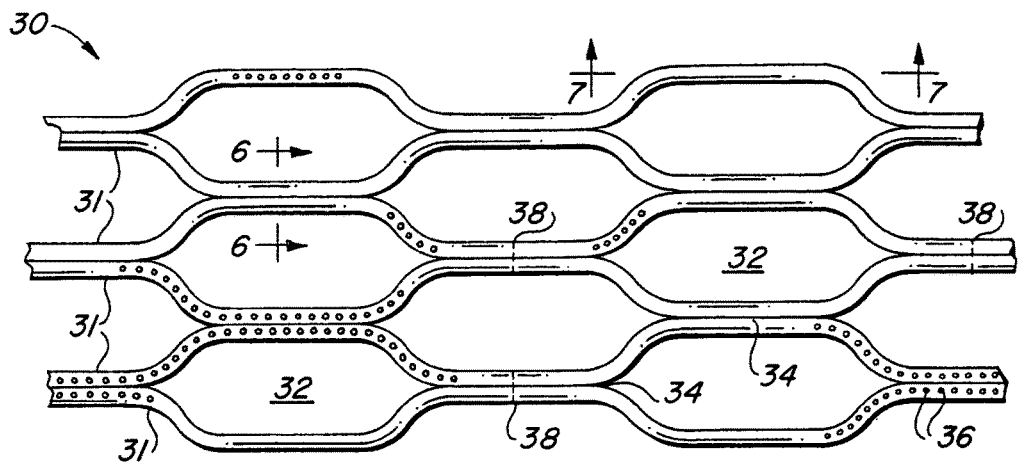
Fig. 5
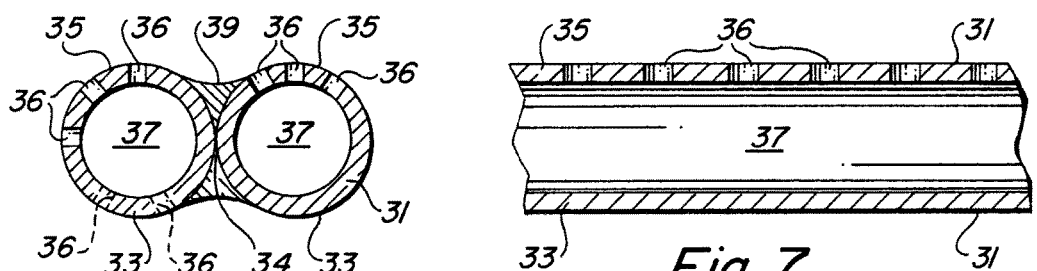
Fig. 6
Fig. 7
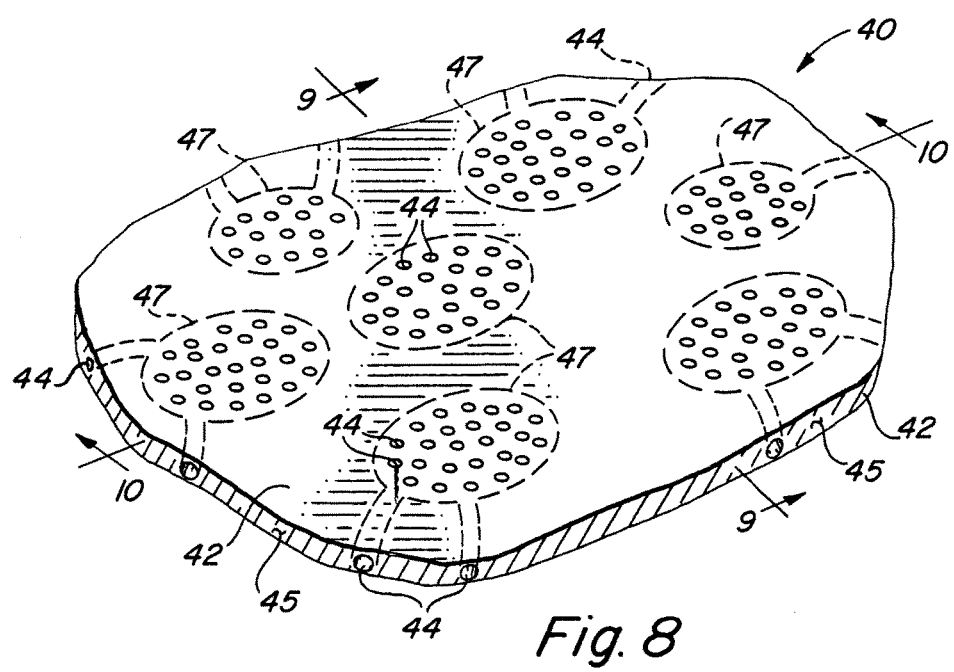
Fig. 8

DEVICE FOR IN VIVO DELIVERY OF BIOACTIVE AGENTS AND METHOD OF MANUFACTURE THEREOF

CROSS-REFERENCE TO RELATED APPLICATIONS

This application is a 371 of PCT/US01/44642 filed Nov. 19, 2001, and PCT/US01/44642 is a CIP of Ser. No. 09/716,146 filed Nov. 17, 2000 U.S. Pat. No. 8,252,044, from which priority is hereby claimed.

BACKGROUND OF THE INVENTION

The present invention relates generally to an implantable device for in vivo delivery of bioactive compounds. The present invention provides an implantable structural material having a three-dimensional conformation suitable for loading a bioactive agent into the structural material, implanting the structural material in vivo and releasing the bioactive agent from the structural agent to deliver a pharmacologically acceptable level of the bioactive agent to an internal region of a body. More particularly, the present invention relates to an implantable medical device, such as an endoluminal stent, stent-graft, graft, valves, filters, occluders, osteal implant or the like, having cavitated regions incorporated within the material of the device with micropores that communicate a bioactive agent from the cavity to an area external the device.

The present invention may be used for any indication where it is desirable to deliver a bioactive agent to a local situs within a body over a period of time. For example, the present invention may be used in treating vascular occlusive disease, disorders or vascular injury, as an implantable contraceptive for delivery of a contraceptive agent delivered intrauterine or subcutaneously, to carry an anti-neoplastic agent or radioactive agent and implanted within or adjacent to a tumor, such as to treat prostate cancer, for time-mediated delivery of immunosuppresents, antiviral or antibiotic agents for treating of autoimmune disorders such as transplantation rejection or acquired immune disorders such as HIV, or to treat implant or non-implant-related inflammation or infections such as endocarditis.

Occlusive diseases, disorders or trauma cause patent body lumens to narrow and restrict the flow or passage of fluid or materials through the body lumen. One example of occlusive disease is arteriosclerosis in which portions of blood vessels become occluded by the gradual build-up of arteriosclerotic plaque, this process is also known as stenosis. When vascular stenosis results in the functional occlusion of a blood vessel the vessel must be returned to its patent condition. Conventional therapies for treatment of occluded body lumens include dilatation of the body lumen using bioactive agents, such as tissue plasminogen activator (TPA) or vascular endothelial growth factor (VEGF) and fibroblast growth factor (FGF) gene transfers which have improved blood flow and collateral development in ischemic limb and myocardium (S. Yla-Herttuala, *Cardiovascular Gene Therapy*, Lancet, Jan. 15, 2000), surgical intervention to remove the blockage, replacement of the blocked segment with a new segment of endogenous or exogenous graft tissue, or the use of a catheter-mounted device such as a balloon catheter to dilate the body lumen or an artherectomy catheter to remove occlusive material. The dilation of a blood vessel with a balloon catheter is called percutaneous transluminal angioplasty. During angioplasty, a balloon catheter in a deflated state is inserted within an occluded segment of a blood vessel and is inflated and deflated a number of times to expand the vessel. Due to the inflation of the balloon catheter, the plaque formed on the vessel walls cracks and the vessel expands to allow increased blood flow through the vessel.

In approximately sixty percent of angioplasty cases, the blood vessel remains patent. However, the restenosis rate of approximately forty percent is unacceptably high. Endoluminal stents of a wide variety of materials, properties and configurations have been used post-angioplasty in order to prevent restenosis and loss of patency in the vessel.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis. To prevent restenosis and thrombosis in the area where angioplasty has been performed, anti-thrombosis agents and other biologically active agents can be employed.

It has been found desirable to deliver bioactive agents to the area where a stent is placed concurrently with stent implantation. Many stents have been designed to delivery bioactive agents to the anatomical region of stent implantation. Some of these stents are biodegradable stents which are impregnated with bioactive agents. Examples of biodegradable impregnated stents are those found in U.S. Pat. Nos. 5,500,013, 5,429,634, and 5,443,458. Other known bioactive agent delivery stents include a stent disclosed in U.S. Pat. No. 5,342,348 in which a bioactive agent is impregnated into filaments which are woven into or laminated onto a stent. U.S. Pat. No. 5,234,456 discloses a hydrophilic stent that may include a bioactive agent adsorbed which can include a biologically active agent disposed within the hydrophilic material of the stent. Other bioactive agent delivery stents disclosed in U.S. Pat. Nos. 5,201,778, 5,282,823, 5,383,927; 5,383,928, 5,423,885, 5,441,515, 5,443,496, 5,449,382, 4,464,450, and European Patent Application No. 0 528 039. Other devices for endoluminal delivery of bioactive agents are disclosed in U.S. Pat. Nos. 3,797,485, 4,203,442, 4,309,776, 4,479,796, 5,002,661, 5,062,829, 5,180,366, 5,295,962, 5,304,121, 5,421,826, and International Application No. WO 94/18906. A directional release bioactive agent stent is disclosed in U.S. Pat. No. 6,071,305 in which a stent is formed of a helical member that has a groove in the abluminal surface of the helical member. A bioactive agent is loaded into the groove prior to endoluminal delivery and the bioactive agent is therefore in direct apposition to the tissue that the bioactive agent treats. Finally, International Application No. WO 00/18327 discloses a drug delivery stent in which a tubular conduit is wound into a helical stent. The tubular conduit has either a single continuous lumen or dual continuous lumens that extend the entire length of the conduit. The tubular conduit has regions or segments thereof that has pores to permit drug "seepage" from the conduit. One end of the tubular conduit is in fluid flow communication with a fluid delivery catheter, which introduces a fluid, such as drug into the continuous lumen and through the pores. Where biodegradable or non-biodegradable polymer-based or polymer-coated stents have been used, the polymers cause an immune inflammatory response once the drug is eluted out of the polymer. Where a polymer is employed as the bioactive agent carrier, it is, therefore, desirable to isolate the polymer from body tissues in order to limit the immune inflammatory response after the bioactive agent has eluted as can be accomplished with the present invention.

SUMMARY OF THE INVENTION

As used herein the term "bioactive agent" is intended to include one or more pharmacologically active compounds which may be in combination with pharmaceutically acceptable carriers and, optionally, additional ingredients such as antioxidants, stabilizing agents, permeation enhancers, and the like. Examples of bioactive agents which may be used in the present invention include but are not limited to hydrophilic agents, hydrophilic agents, antiviral drugs, antibiotic drugs, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, immunosuppresents, such as rapomycin, beta and calcium channel blockers, genetic materials including DNA and RNA fragments, complete expression genes, antibodies, lymphokines, growth factors (vascular endothelial growth factor (VEGF) and fibroblast growth factor (FGF)), prostaglandins, leukotrienes, laminin, elastin, collagen, nitric oxide (NO) and integrins.

The inventive structural material has a three dimensional conformation having a geometry and construction in which there is an internal cavity or a plurality of internal cavities within the structural material and a conduit or opening or plurality of conduits or openings which communicate between the internal cavity and external the structural material. The three dimensional conformation of the structural material may assume a cylindrical, tubular, planar, spherical, curvilinear or other general shape which is desired and suited for a particular implant application. For example, in accordance with the present invention there is provided an endoluminal stent that is made of a plurality of structural members that define a generally tubular shape for the endoluminal stent. At least some of the plurality of structural members are comprised of the inventive structural material and have at least one internal cavity and at least one conduit or opening which communicates between the internal cavity and external the stent. Alternate types of implantable devices contemplated by the present invention include, without limitation, stent-grafts, grafts, heart valves, venous valves, filters, occlusion devices, catheters, osteal implants, implantable contraceptives, implantable antitumor pellets or rods, or other implantable medical devices.

The inventive stent for delivery of bioactive agents consists generally of a plurality of structural elements, at least some of which have internal cavities that retain the bioactive agents, and openings that pass between the internal cavities and the surface of the structural elements to communicate the bioactive agent from the internal cavity external the stent. Other than described herein, the present invention does not depend upon the particular geometry, material, material properties or configuration of the stent.

Because of their use as a structural scaffold and the requirement that stents be delivered using transcatheter approaches, stents necessarily are delivered in a reduced diametric state and are expanded or allowed to expand in vivo to an enlarged diametric state. Thus, all stents have certain structural regions that are subject to higher stress and strain conditions than other structural regions of the stent. Thus, it may be advantageous to position the internal cavities that retain the bioactive agents in structural regions of the stent that are subjected to relatively lower stress and strain during endoluminal delivery and deployment. Alternatively, where delivery of a bolus of a bioactive agent is desired, internal cavities may be positioned in regions that undergo large deformation during delivery and deployment thereby forcing the bioactive agent out of the internal cavity under the positive pressure exerted by the deformation. Diffusion forces, then, elute remaining bioactive agent present in either the region of large deformation or the regions of lower stress and strain.

BRIEF DESCRIPTION OF THE DRAWINGS

FIG. 1 is a perspective view of an implantable member in accordance with the present invention.

FIG. 2 is a perspective view of an endoluminal stent having a plurality of structural members in accordance with the present invention.

FIG. 3 is a cross-sectional view taken along line 3-3 of FIG. 2.

FIG. 4 is a cross-sectional view taken along line 4-4 of FIG. 2.

FIG. 5 is a fragmentary perspective view of an alternative embodiment of the inventive endoluminal stent in accordance with the present invention.

FIG. 6 is a cross-sectional view taken along line 6-6 of FIG. 5.

FIG. 7 is a cross-sectional view taken along line 7-7 of FIG. 5.

FIG. 8 is a perspective view of a planar structural element for delivery of a bioactive agent in accordance with the present invention.

DETAILED DESCRIPTION OF THE PREFERRED EMBODIMENTS

Figure 9:
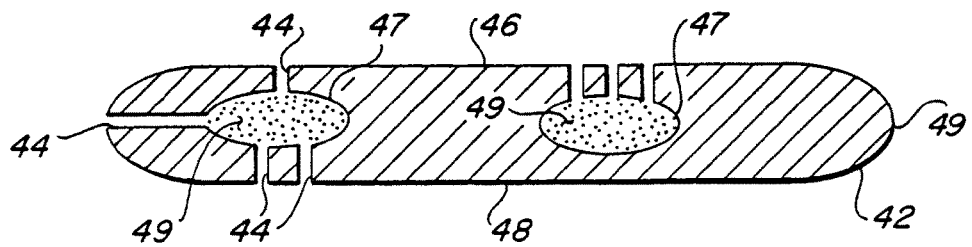
FIG. 9 is a cross-sectional view taken along line 9-9 of FIG. 8.

As noted above, the term "bioactive agent" is intended to encompass one or more pharmacologically active compounds which may be in combination with pharmaceutically acceptable carriers and, optionally, additional ingredients such as antioxidants, stabilizing agents, permeation enhancers, and the like. Examples of bioactive agents which may be used in the present invention include but are not limited to antibiotic drugs, antiviral drugs, neoplastic agents, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, immunosuppresents, such as rapomycin, beta and calcium channel blockers, genetic materials including DNA and RNA fragments, complete expression genes, antibodies, lymphokines, growth factors (vascular endothelial growth factor (VEGF) and fibroblast growth factor (FGF)), prostaglandins, leukotrienes, laminin, elastin, collagen, nitric oxide (NO), and integrins.

With particular reference to FIG. 1, the present invention consists generally of a body element 10 having a three-dimensional conformation defining X, Y and Z-axes of the body element 10 and at least one of a plurality of interior cavities 12 defined within the body element 10, and at least one of a plurality of passages or pores 14 which communicate between the at least one of a plurality of interior cavities 12 and exterior to the body element 10. While the body element 10 depicted in FIG. 1 is of a generally cylindrical three dimensional conformation, alternative three dimensional conformations, such as planar, spherical, ovular, tetrahedral, curvilinear or virtually any other three dimensional conformation suitable for implantation into a living body is contemplated by the present invention. The plurality of passages 14 have dimensions sufficient to permit the bioactive agent to elute by diffusion, osmotic pressure or under the influence of a positive pressure applied by cellular in-growth into the plurality of interior cavities 12.

The location of the plurality of passages 14 is dependent upon the particular application for which the body element 10 is intended. For example, with particular reference to FIGS. 2-5, where the body element 10 is a tubular body 20 made of a plurality of interconnected structural elements 21, such as a stent, stent-graft or graft, which defines a central lumen 22 and has openings 24 at opposing proximal and distal ends of the tubular body 20, the plurality of passages 14 are formed in at least some of the plurality of interconnected structural elements 21 and may be disposed on only the luminal surface 26 or only on the abluminal surface 28 of the tubular body 20, or both. Pores 14 on the luminal surface 26 only will communicate the bioactive agent into the lumen and any body fluid, such as blood, flowing through the central lumen of the tubular body, while pores 14 on only the abluminal surface 26 will communicate the bioactive agent to the abluminal surface of the tubular body. At least a portion of some of the plurality of interior cavities 12 may communicate with either the proximal or distal ends of at least some of the plurality of interconnected structural elements 21. In this case, the proximal and/or distal ends of at least some of the plurality of interconnected structural elements may be tapered such as to self-cannulating into body tissue during delivery and deployment. The bioactive agent retained with the internal cavity 12 which communicates with the proximal and/or distal ends of at least some of the plurality of interconnected structural elements will then pass out of the proximal and/or distal ends in much the same manner as fluid flowing through an injection needle.

In addition to the foregoing positioning of the pores 14, both the plurality of internal cavities 12 and the plurality of pores 14 may be positioned to be discontinuous and in different circumferential or different longitudinal regions of the tubular body 20. Within a single one of the plurality of interconnected structural elements 21, the internal cavities 12 may be separated by a separation member 25, which completely subtends the internal cavity 12, divides it into discrete discontinuous internal cavities 12. The advantage of forming a plurality of discontinuous internal cavities 12 is that it permits loading of different bioactive agents into different regions of the body member 10 or tubular member 20 to isolate different regions for delivery of different bioactive agents to different sites within a body. For example, a first grouping of a plurality of internal cavities 12 and associated plurality of pores 14 may be located at a proximal end of the tubular body 20, and a second grouping of a plurality of internal cavities 12 and associated plurality of pores 14 may be located at an intermediate region of the tubular body 20, and a third grouping of a plurality of internal cavities 12 and associated plurality of pores 14 may be located at a distal end of the tubular body 20. A first bioactive agent may be loaded into the first and third grouping of a plurality of internal cavities 12, while a second bioactive agent may be loaded into the second grouping of a plurality of internal cavities 12. Where, for example, the tubular body 20 is an endoluminal stent, stent-graft or graft which is implanted post-angioplasty, the proximal and distal ends of the tubular body 20 are anchored adjacent to healthy tissue while the intermediate region of the tubular body 20 are positioned adjacent to the diseased or injured tissue. In this configuration, a first bioactive agent, such as an endothelial growth factor and/or contrast medium to impart enhanced radioopacity to the tubular body 20 may be carried in the first and third groups of a plurality of internal cavities 12 and associated pores 14, while an anticoagulant, such as heparin, may be carried in the second group of a plurality of internal cavities 12 and associated pores 14. In this manner, the tubular body has enhanced radioopacity to aid in delivery and deployment and endothelial growth factors to enhance endothelialization of the tubular body 20, while delivering an anticoagulant directly to the site of the tissue lesion.

Moreover, where the internal cavities 12 are discontinuous, the plurality of pores 14 may be configured to include degradable plugs which degrade at different rates to expose different bioactive agents in the internal cavities 12 to the body at different points in time. Alternatively or additionally, the degradable plugs may degrade at different to expose the same bioactive agent in different internal cavities 12 at different periods of time to effectively elongate the period of time during which the bioactive agent is delivered. Alternatively, the plurality of pores 14 may be dimensioned to permit different elution rates of the bioactive agent and provide for a more protracted or time-release of the bioactive agent from the internal cavities 12. Moreover, by adjusting the carriers of the bioactive agent, e.g., to provide more or less capacity to elute in vivo, in combination with alternate dimensions and orientations of the plurality of pores 14, e.g., luminal or abluminally oriented, both the time of elution and the duration of elution may be adjusted.

The body element 10 is preferably formed of a metal such as titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, or stainless steel.

Turning to FIGS. 5-7 there is illustrated an alternative embodiment of the inventive endoluminal stent fabricated from a plurality of tubular structural elements 31 formed into a tubular stent and having a desired geometry. It will be appreciated that the generally hexagonal cell geometric pattern illustrated in FIG. 5 is merely exemplary and a myriad of different geometries of different geometric complexities are contemplated by the invention. Each of the tubular structural elements 31 has a central lumen 37 that forms the internal cavity within each structural element 31. A plurality of separation member 38 may be provided to subdivide the internal cavity 37 into a plurality of discontinuous internal cavities 37. Each of the tubular structural elements 31 has a plurality of openings 36 which communicate between the internal cavity 37 and one or both of a luminal surface 33 or an abluminal surface 35 of each of the plurality of tubular structural elements 31. The tubular structural elements 31 may assume any transverse cross-sectional configuration having a central lumen.

Those of ordinary skill in the stent forming arts will understand that in order to form a tubular endoluminal stent of tubular elements 31, it is necessary to join at least some of the plurality of tubular elements 31. Conventionally, a plurality of spot-welds 39 which serve to interconnect sections of individual tubular elements 31 in juxtaposed relationship 34 to one and other. The interconnected sections of individual tubular elements 31 are joined in such a manner as to create open interstices 32 between adjacent pairs of interconnected sections of individual tubular elements 31. The plurality of spot welds 39 may also be employed to seal the internal cavity 37 at the position of the spot weld 39, thereby creating a separation member 38 within the internal cavity 37 of each individual tubular element 31 and forming a discontinuous internal cavity 37.

As noted above, the plurality of openings 36 are dimensioned to permit the bioactive agent to elute from the at least one of a plurality of internal cavities 37 and through the associated plurality of openings 36 by diffusion, osmotic pressure or under the influence of a positive pressure applied by cellular in-growth into the plurality of internal cavities 37 or under positive pressure applied by stress and/or strain exerted on the plurality of internal cavities 37 due to deformation of the individual tubular structural elements 31. Additionally, the positioning of the plurality of openings 36 relative to the individual tubular structural elements 31 and to the endoluminal stent as a whole may be adapted to deliver varying quantities of or different bioactive agents from different regions of the tubular structural elements 31 or different regions of the endoluminal stent 30. Moreover, proximal and/or distal ends of individual tubular structural elements 31 may be tapered so as to form self-cannulating ends of the individual tubular structural elements 31 which penetrate body tissue and permit the bioactive agent to be communicated from the internal cavity 37 out the proximal or distal end of the tubular structural element 31 in a manner similar to a hypodermic needle.

Figure 10:
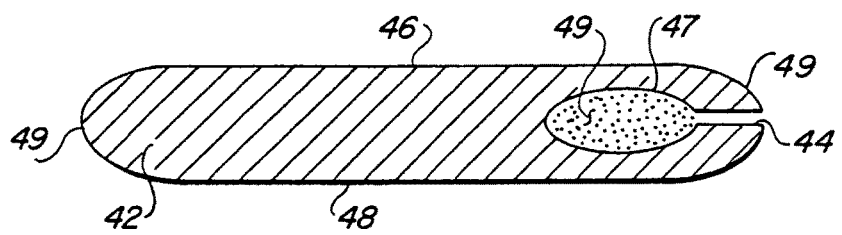
FIG. 10 is a cross-sectional view taken along line 10-10 of FIG. 8.

In accordance with another embodiment of the present invention, and as illustrated in FIGS. 8-10, there is provided an implantable device 40 which consists of a structural body 42 having a three-dimensional conformation extending in the X-axis, Y-axis and Z-axis dimensionally. While the illustrated embodiment of the structural body 42 is planar, those of ordinary skill in the medical device fabrication art will understand that it is within the skill of the artisan to fabricate the structural body 42 of any desired three-dimensional conformation depending upon the desired use and indication of the implantable device 40. The three-dimensional conformation of the structural body 42 may be cylindrical, tubular, quadrilinear, planar, spherical, ovular, tetrahedral, curvilinear or virtually any other three-dimensional conformation suitable for implantation into a living body.

Like the above-described embodiments, the structural body 42 has at least one of a plurality of internal cavities 47, each of which carry a bioactive agent 49, and a plurality of openings 44 which pass from at least one upper 46, lower 48 or lateral 45 surface of the structural body 42, through the Z-axis thickness of the body and communicate with the at least one of a plurality of internal cavities 47 in the structural body 42. Where a plurality of internal cavities 47 are provided within the structural body 42, a plurality of bioactive agents 49 may be loaded into the structural body 42 with one or more bioactive agents 49 being loaded into each of the plurality of internal cavities 47.

Each of the above-described preferred embodiments of the present invention may be fabricated by a number of methods. In accordance with present invention, it is contemplated that either forming wrought metal parts, such as capillary tubing, into the implantable device or forming the implantable devices by vacuum deposition techniques are the preferred method of making the implantable structural elements of the present invention. Where an implantable device is to be fabricated of a plurality of individual tubular elements, such as depicted in FIGS. 5-7, pre-existing microtubular members having an outer diameter, for example, between 60 and 400 m and a wall thickness of between 10 and 350 m, may be employed to fabricate extremely small dimensioned devices suitable for intracranial or coronary artery applications. The microtubular members may be formed into a cylindrical endoluminal device, such as by braiding or bending and joining microtubular members together by spot welding. Where ends of the microtubular members are formed to be self-cannulating, the self-cannulating ends may be exposed on the abluminal surface of an endoluminal device at any point along the longitudinal axis thereof. The plurality of openings passing through the wall of each of the individual tubular elements may be formed by microdrilling the openings through the wall and into the internal cavity or lumen of the individual tubular members. The plurality of openings may be laser cut, etched or formed by EDM methods, and may be formed either pre- or post-formation of the tubular elements into the three-dimensional conformation of the implantable device. Where an implantable device is to be formed from non-preexisting structural elements, vacuum deposition techniques may be employed to form the implantable structural body, such as sputtering, reactive ion etching, chemical vapor deposition, plasma vapor deposition, or the like, as are known in the microelectronics fabrication arts and are more fully described in co-pending, commonly assigned U.S. patent application Ser. No. 09/443,929, filed Nov. 19, 1999, which is hereby incorporated by reference. Because, the internal cavities and openings must be formed during deposition, the vacuum deposition techniques must be modified to deposit requisite patterns of sacrificial material to form the regions of the internal cavities and openings, over a base layer of structural material, then depositing a second layer of structural material over the sacrificial material and the base layer. The sacrificial material may then be removed, such as by etching, to leave the internal cavities and plurality of openings formed within the deposited bulk material.

Figure 11:
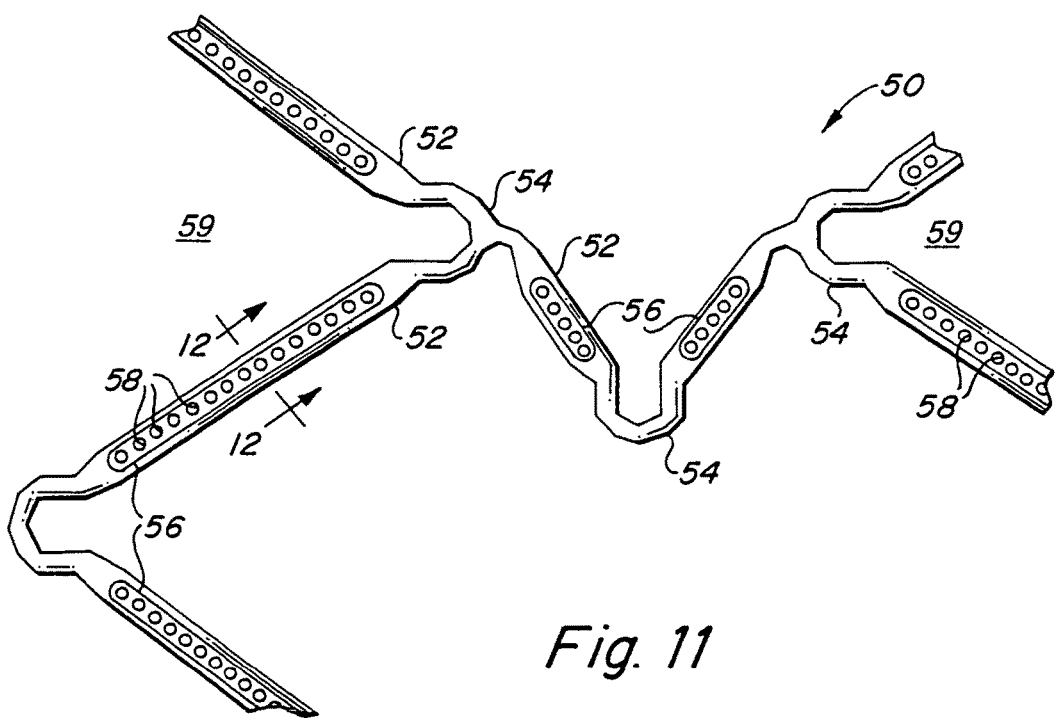
FIG. 11 is a plan view of an alternative embodiment of the endoluminal stent in accordance with the present invention.
Figure 12:
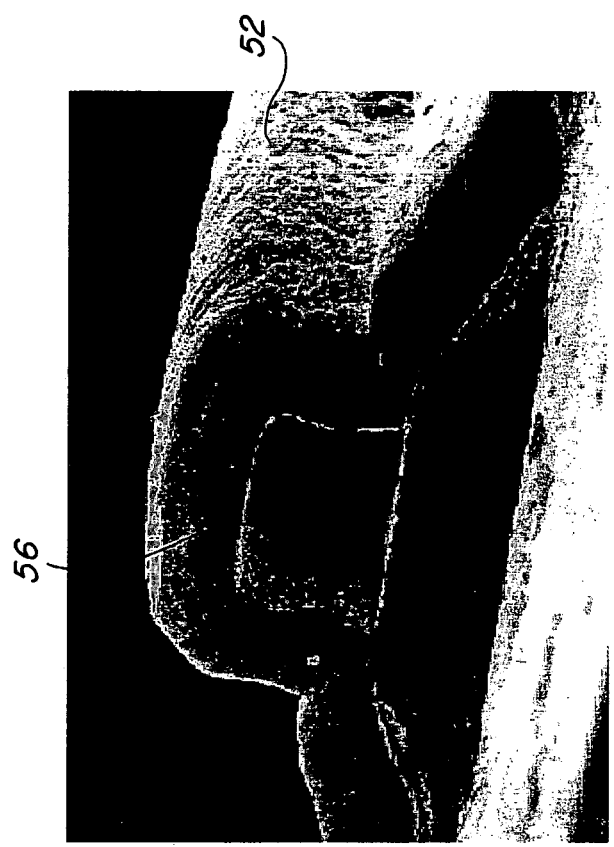
FIG. 12 is a photomicrographic cross-sectional view taken along line 12-12 of FIG. 11.

An alternative embodiment of the present invention is illustrated in FIGS. 11 and 12, in which an endoluminal stent configuration is depicted for example only. Those of ordinary skill in the art will understand and recognize that alternative device designs and geometries are also contemplated by the present invention. In accordance with the alternate embodiment of the invention there is illustrated an endoluminal stent 50 comprised of a plurality of structural elements 52 interconnected at a plurality of hinge regions 54 and defining a plurality of interstices 59 bounded by the plurality of structural elements and the plurality of hinge regions 54. As described above, the material used to fabricate the inventive device has a Z-axis wall thickness in the device material. The inventive device incorporates at least one of a plurality of internal cavities 56 within the wall thickness of the material used to form the implantable device or endoluminal stent 50. A plurality of micropores 58 are provided and communicate between a external surface of the device 50 and one of the plurality of internal cavities 56. As noted above, the plurality of micropores 58 are dimensioned to permit the bioactive agent to elute from the at least one of a plurality of internal cavities 56 and through the associated plurality of micropores 58 by diffusion, osmotic pressure or under the influence of a positive pressure applied by cellular in-growth into the plurality of internal cavities 56 or under positive pressure applied by stress and/or strain exerted on the plurality of internal cavities 56 due to deformation of the individual structural elements 52. The plurality of micropores 58 may furthermore be provided to communicate between an internal cavity 56 and either a luminal or abluminal surface of the inventive endoluminal stent, such as to expose the bioactive agent retained within the plurality of internal cavities 56 either to the blood stream, in the case of luminal micropores 58, and/or to adjacent tissue, in the case of abluminal micropores 58.

The at least one of a plurality of internal cavities 56 may be continuous or discontinuous throughout the inventive device 50. Specifically, in accordance with one preferred embodiment of the invention, the plurality of internal cavities 56 is discontinuous and each of the plurality of discontinuous internal cavities 56 reside within regions of the device 50 that are substantially non-load bearing regions of the device. In the particular embodiment illustrated in FIG. 11, the plurality of hinge regions 54 are devoid of internal cavities 56 because they are load bearing regions of the stent. It is contemplated, however, that regions of the inventive device 50 that are deformed or that are load bearing may include either continuous internal cavities 56 or discontinuous internal cavities within their wall thickness and provide for elution of a bioactive agent retained within the internal cavity positioned at the load bearing region under the influence of a positive motivating pressure exerted on the bioactive agent by deformation or load stress transferred by the device geometry to the internal cavity and to the bioactive agent. By providing regions of continuous and discontinuous internal cavities 56, a plurality of bioactive agents may be loaded into different internal cavities 56 for achieving different elution rates and pharmacological effects. FIG. 12 is a photomicrograph illustrating a transverse cross-sectional view through an individual structural element 52 illustrating the internal cavity 56.

Figure 13A:
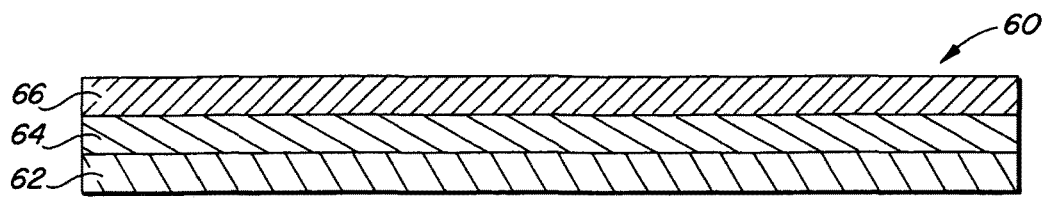
FIGS. 13A-13F are sequential diagrams illustrating the inventive method for fabricating the inventive endoluminal stent.
Figure 13B:
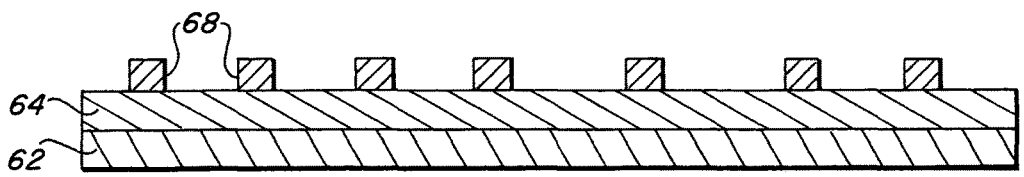
Figure 13C:
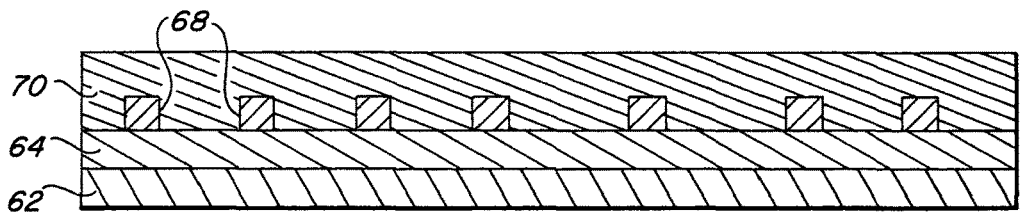
Figure 13D:
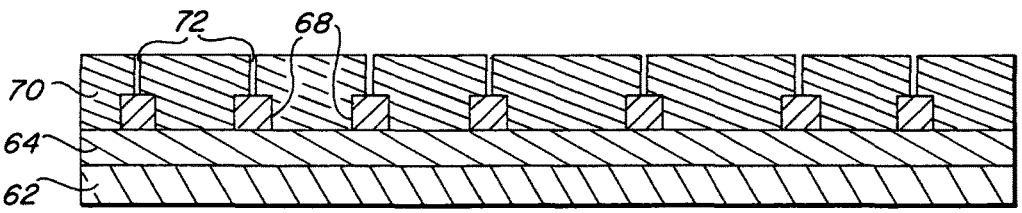
Figure 13E:
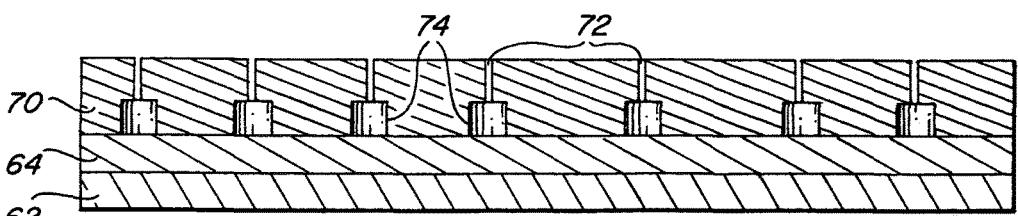
Figure 13F:
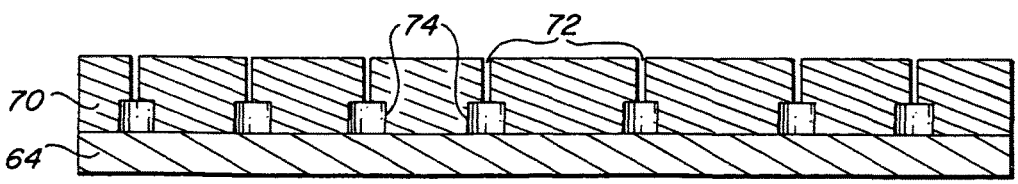
Figure 14:
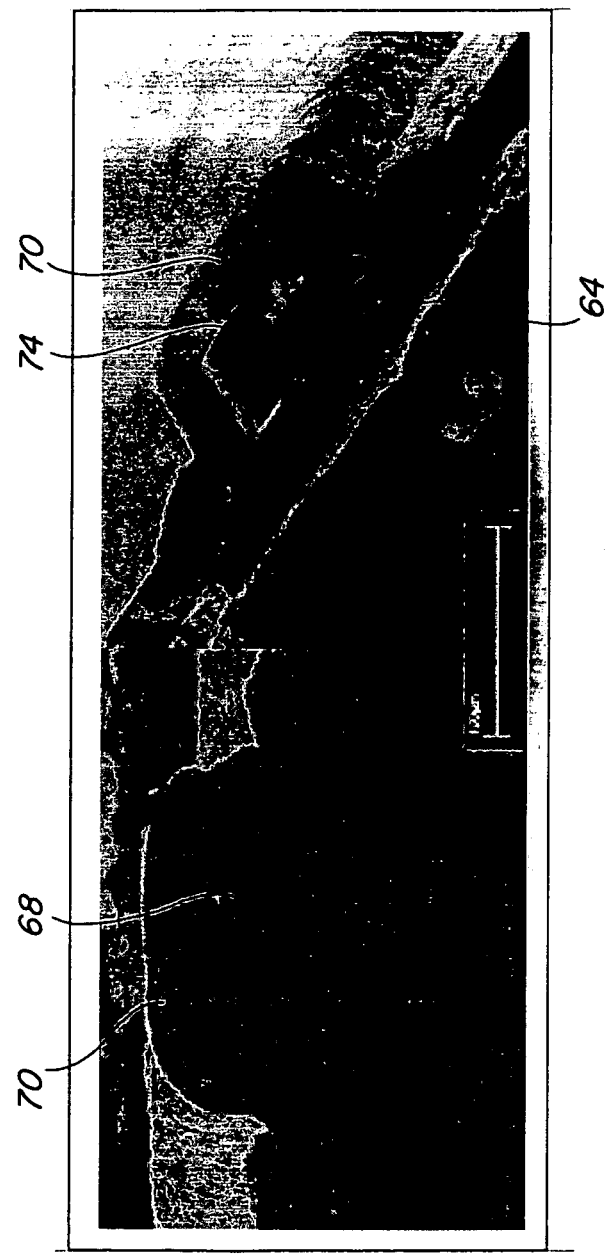
FIG. 14 is are side-by-side photomicrographs illustrating selective formation of an internal cavity within the inventive endoluminal stent.

Turning now to FIGS. 13A-F and 14 there is depicted a method 60 for fabricating the inventive devices for delivery of bioactive agents. In FIG. 13A a first layer 64 of a device-forming metal, such as titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, or stainless steel is formed onto a sacrificial substrate material 62. A sacrificial layer 66 is formed of a sacrificial material capable of being selectively removed without removing the underlying first layer 64. The next step involves selective removal of portions of the sacrificial layer 66 to leave cavity-forming portions 68 of the first sacrificial layer 66. A second layer 70 of a device forming metal, such as those enumerated above, is then formed onto the first layer 62 of the device forming metal and covers the cavity-forming portions 68. In the next step, depicted in FIG. 13D, the plurality of micropores 72 are formed and pass through the second layer 70 and communicate with the cavity-forming portions 68. The plurality of micropores 72 may be formed by selective removal of the second layer 70 such as by laser or chemical etching. Alternatively, the second layer 70 of the device forming metal may be selectively formed such as to form the plurality of micropores 72 during forming of the second layer 70. In the next step, depicted in FIG. 13E, the sacrificial material of the cavity-forming portions 68 is selectively removed, such as by chemical etching of the cavity-forming portions 68, without removing or effecting the material properties of either the first layer 64 or the second layer 70 of the device material, thereby leaving a plurality of internal cavities 74 defined within the second layer 70 and bounded by the first layer 64 of device material, with the plurality of micropores 72 communicating between the plurality of internal cavities 74 and an external surface of the second layer 70 of the device material 70. Finally, in step 13F, the sacrificial substrate material 62 is selectively removed thereby obtaining the inventive implantable device. FIG. 14 is a photomicrograph illustrating a device formed in Step 13E at the left panel and in Step 13F in the right panel.

In accordance with a preferred embodiment of the present invention, the above method is performed by vacuum deposition techniques to form the inventive implantable device. Suitable processed, include, for example, sputtering, reactive ion etching, chemical vapor deposition, plasma vapor deposition, or the like, as are known in the microelectronics fabrication arts and are more fully described in co-pending, commonly assigned U.S. patent application Ser. No. 09/443,929, filed Nov. 19, 1999, which is hereby incorporated by reference.

It will be understood by those of ordinary skill in the art that alternative designs of implantable devices, for example grafts, patches, shunts, valves, filters or occluders, that do not require structural elements 52, hinge regions 54 or interstices 59 of an endoluminal stent, yet have a device material with a Z-axis thickness that is suitable for incorporation of the internal cavities and micro-openings or micropores of the present invention to elute a bioactive agent.

Regardless of which fabrication method is employed, the bioactive agent must be loaded into the internal cavities of the implantable device. Loading of the bioactive agent may be accomplished by flowing a liquid or semi-liquid state of the bioactive agent through the plurality of openings and into the internal cavities, either throughout the entire device or in regions of the implantable device. Flow loading may be facilitated by applying positive pressure, temperature change or both, such as is used in hot isostatic pressing (HIP). In HIP the pressurizing medium is typically a gas, and the process is carried out at elevated temperatures for specific time periods. While HIP is typically utilized to densify materials, to heal casting defects and voids, or to bond similar or dissimilar materials it may be used to drive a fluid or semi-fluid from external the implantable device into the internal cavities of the implantable device. Alternative, diffusion-mediated loading, osmotic loading or vacuum loading may be employed to load the bioactive agent into the internal cavities.

While the present invention has been described with reference to its preferred embodiments, those of ordinary skill in the art will understand and appreciate that variations in structural materials, bioactive agents, fabrication methods, device configuration or device indication and use may be made without departing from the invention, which is limited in scope only by the claims appended hereto.

What is claimed is:

1. An endoluminal stent for delivering a bioactive agent to a situs in a body comprising:
    a radially expandable cylindrical member formed of a plurality of undulating hollow members, each of the plurality of undulating hollow members abutting a portion of an adjacent undulating hollow member and each of the plurality of undulating hollow members being joined to an adjacent undulating hollow member;
    a continuous void space formed entirely within at least one of the plurality of undulating hollow members, wherein the continuous void space is bounded by internal wall surfaces of the at least one of a plurality of undulating hollow tubular members, the internal wall surface having a thickness;
    a plurality of pores formed in and passing through an external wall surface and internal wall surface thickness of at least one of the plurality of undulating hollow tubular members and communicating between the continuous void space and the external wall surface and being open to an exterior surface of the radially expandable cylindrical element, further wherein each of the pores has a cross section smaller than a smallest cross section of the continuous void space; and at least one bioactive agent retained within the continuous void space and elutable through the plurality of pores.

2. The endoluminal stent of claim 1, further comprising a plurality of welds connecting portions of the plurality of undulating hollow members.

3. The endoluminal stent according to claim 1, wherein the plurality of undulating hollow members further comprises a material selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, nitinol, and stainless steel.

4. The endoluminal stent according to claim 1, wherein the at least one bioactive agent comprises a pharmacologically active agent selected from the group consisting of hydrophobic pharmacologically active agents, hydrophilic pharmacologically active agents, antibiotic drugs, antiviral drugs, neoplastic agents, steroids, fibronectin, anticlotting drugs, anti-platelet function drugs, drugs which prevent smooth muscle cell growth on inner surface wall of vessel, heparin, heparin fragments, aspirin, coumadin, tissue plasminogen activator, urokinase, hirudin, streptokinase, antiproliferatives, antioxidants, antimetabolites, thromboxane inhibitors, non-steroidal and steroidal anti-inflammatory drugs, immunosuppresents, rapamycin, beta and calcium channel blockers, genetic materials including DNA and RNA fragments, complete expression genes, antibodies, lymphokines, growth factors, prostaglandins, leukotrienes, laminin, elastin, collagen, nitric oxide, and integrins.

5. The endoluminal stent according to claim 1, wherein the plurality of undulating hollow members further comprise a vacuum deposited metal.

6. The endoluminal stent of claim 1 wherein, each undulating hollow member includes a first structural region and a second structural region, further wherein the first structural region is subjected to relatively lower stress or strain forces than second structural region upon radial expansion of the radially expandable cylindrical member.

* * * * *